United States Patent [19]

Gerow

[11] Patent Number: 4,690,135

[45] Date of Patent: Sep. 1, 1987

[54] MALE IMPOTENCE PROSTHESIS

[75] Inventor: Frank J. Gerow, Houston, Tex.

[73] Assignee: Synergist Limited, Houston, Tex.

[21] Appl. No.: 859,459

[22] Filed: May 5, 1986

[51] Int. Cl.⁴ .............................................. A61F 5/41
[52] U.S. Cl. ..................................................... 128/79
[58] Field of Search ................... 128/79; 604/347, 349

[56] References Cited

U.S. PATENT DOCUMENTS

| | | | |
|---|---|---|---|
| 2,358,440 | 9/1944 | Bowman | 128/79 |
| 2,577,345 | 12/1951 | McEwen | 128/79 |
| 3,683,901 | 8/1972 | Wegener | 128/79 |
| 3,820,533 | 6/1974 | Jones | 128/79 |
| 4,175,554 | 11/1979 | Gerow | 128/79 |
| 4,378,008 | 3/1983 | Osbon | 128/79 |

FOREIGN PATENT DOCUMENTS

| | | | |
|---|---|---|---|
| 938465 | 10/1963 | United Kingdom | 604/349 |
| 1497441 | 1/1978 | United Kingdom | 128/79 |

Primary Examiner—Robert P. Swiatek
Assistant Examiner—Cary E. Stone
Attorney, Agent, or Firm—Darryl M. Springs

[57] ABSTRACT

In an external device for receiving and positioning the male penis in a simulation of an erection to overcome impotence, which includes a flexible hollow cylindrical body enclosed at one end and having the other end open for receiving inserting the penis with a tube provided for introducing a negative pressure in the interior of the body for drawing the penis into the body to its anatomic limit to achieve an erection, the improvement comprising a sealing member integrally extending from the open end of the cylindrical body and comprising a thin-walled flexible sleeve-like sealing portion having a predetermined substantially constant inner circumferential measurement which is a function of the circumference of the stretched non-erect penile shaft, the predetermined inner circumferential measurement being less than the inner circumferential measurement of the cylindrical body for functioning as a seal about the penile shaft to maintain the negative pressure introduced therein, but not engaging the penile shaft tightly enough to restrict venous blood flow therein, and a flexible transition portion integrally interconnecting one end of the sleeve-like sealing portion and the open end of the body for positioning the sleeve-like sealing portion in concentric axial alignment with the cylindrical body.

8 Claims, 8 Drawing Figures (INVENTION)

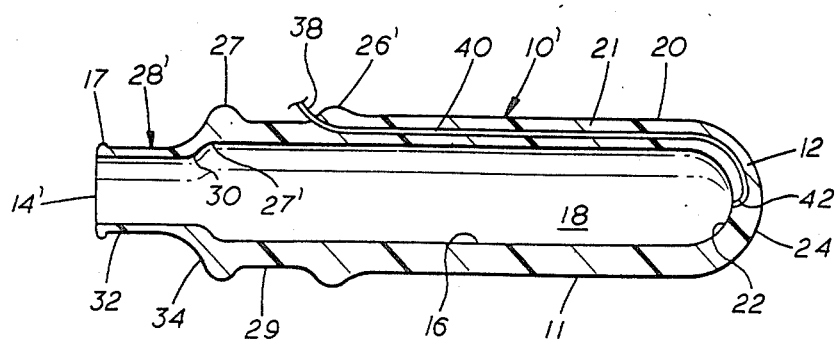
FIG. 6 (INVENTION)
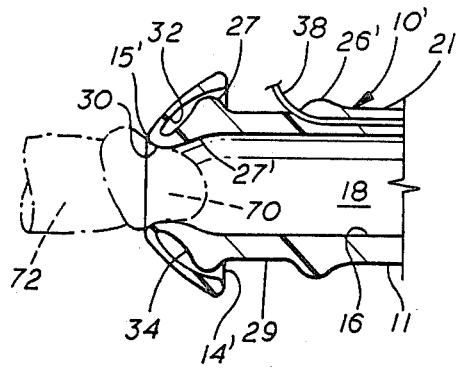
FIG. 7 (INVENTION)
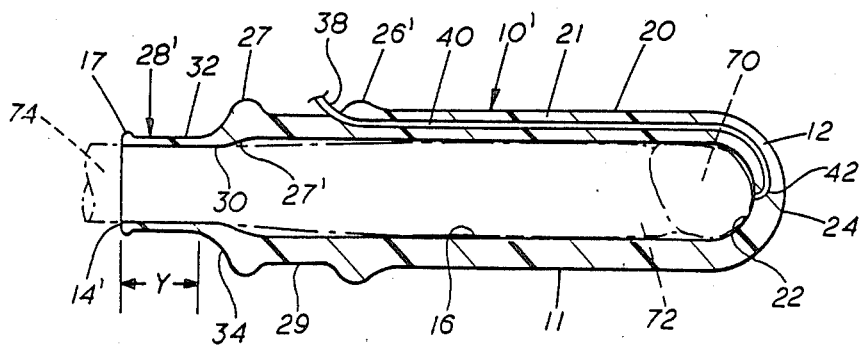
FIG. 8 (INVENTION)

MALE IMPOTENCE PROSTHESIS

BACKGROUND OF THE INVENTION

The present invention relates to an improvement in a device for receiving the penis of a totally impotent male and positioning it in a simulation of an erection for facilitating sexual intercourse. More specifically, the present invention relates to an improved thin-walled seal in the device that encircles and contacts the penis for maintaining a negative pressure within the device.

In the prior art, various solutions have been attempted to aid impotent males in producing or simulating an erection. One such solution is directed to the teaching that pressure applied in various ways at the base of the penis will obstruct venous return from that organ and thereby facilitate or enhance penile erection. Other prior art methods teach the use of splint-type devices, with open sides and longitudinally running stiff members usually covered with a rubber sleeve to facilitate erection of the male organ and the ability of the user to penetrate during sexual intercourse.

Still another method used in the prior art teaches use of at least a single longitudinal member with circumferential loops positioned to receive and hold the penis in an erect state. Yet another prior art device is that which utilizes a hollow cylindrical body having an enclosed extremity and a duct permitting communication between the inside of the hollow body, at a position adjacent to the closed end, and the outside. Additionally, the open end is provided with a circular rigid constrictor which imparts pressure to restrict venus return similar to that above-described for other prior art devices. In this device, as the penis is inserted into the interior of the hollow body, air is forced out of the interior through the duct, forcing a one-way valve positioned therein to open. Further, this described device assumes that the user must be able to achieve enough penis rigidity to drive the penis through the constriction ring at the open end to produce any effective pressure change inside the hollow body and thereby actuate the valve to permit the penis to advance further. An impotent male with a flaccid penis cannot achieve insertion into the disclosed device, since insertion is achieved against the higher pressure of the air compressed in the interior of the device. Also, since the constriction at the open end is to be tight enough to produce restriction in blood flow, a totally impotent male can never achieve enough of an erection to introduce the penis through the open end.

The inventor has received a prior patent, U.S. Pat. No. 4,175,554 entitled "Prosthesis of Male Impotence" which discloses a device for receiving and positioning in a simulation of an erection the penis of an impotent male, which device comprises a sleeve-like body enclosed at one end and having the other end open for receiving the extremity of the penis. After the penis is inserted, means is provided for introducing a negative pressure in the interior of the body which has the effect of drawing the penis into the interior of the sleeve to achieve an erection-like condition. The open-end of the sleeve-like body terminates in a thin-walled section, of the same inner diameter as the remainder of the sleeve-like body, to snugly fit the erect penis and act as a seal for preserving the interior negative pressure but not to constrict blood flow.

However, it has been discovered that when the above-described device is used, in the vast majority of cases the shaft diameter of the penis in the area of the thin-walled section of the device adjacent to the penis base does not enlarge as much as the more distal end of the penis shaft. This failure to enlarge as expected has permitted the thin-walled seal to fail, thereby equalizing the pressure inside and outside the device and losing the penile erection. However, the prior patented prosthesis still works when the stretched non-erect circumference and the erect circumference are the same, but has a limited utility because of the limited percentage of cases when this occurs.

The present invention overcomes the deficiencies of the prior art by providing an improved sealing member in a flexible sleeve-like penile erection assistance device for insuring a positive seal without restricting venous blood flow.

BRIEF SUMMARY OF THE INVENTION

An improved device for treating male impotence is disclosed that includes a generally cylindrical hollow body member having a first predetermined substantially constant inner circumferential measurement and constructed of a flexible and elastic material, the body member having a distal closed end and a proximal open end for permitting insertion of a male penis, a sealing member integrally extending from the proximal open end of the body member and comprising a thin-walled flexible sleevelike sealing portion having a second predetermined substantially constant inner circumferential measurement which is less than the first predetermined inner circumferential measurement of said body member, a flexible transition portion integrally interconnecting one end of the sleeve-like sealing portion and the open proximal end of the body member for positioning the sleeve-like sealing portion in concentric axial alignment with the body member, the transition portion providing a radiused circumferential shoulder extending axially from the one end of the sleeve-like sealing portion and flaring outwardly to an increased diameter to join the open proximal end of the body member. The sleeve-like sealing portion is adapted to be rolled up over the transition portion and the proximal end of the thicker-walled body member to permit the distal end of a male penis to engage the inner walls of the hollow body member. The second predetermined substantially constant inner circumferential measurement of the sleeve-like sealing portion is selected for snugly engaging the penile shaft for functioning as a seal about the male penis when said sealing portion is returned to its unrolled extended position, but not engaging the penile shaft tightly enough to restrict venous blood flow. The device also includes a length of flexible tubing at least a portion of which is disposed longitudinally in the wall of the body member, one end of the tubing communicating with the most distal end of the interior of the hollow body member, the other end of the tubing freely extending from the body member for permitting the evacuation of the air in the interior of the hollow body member forward of the engaged male penis for exerting a negative pressure therein for drawing the male penis to its anatomic limit into the interior of the hollow body member for achieving an erection therein.

In accordance with another principle of the invention the radiused circumferential shoulder of the transition portion has a radius of sufficient size for providing a smooth rounded surface that will not injure the erect penis.

In accordance with another principle of the invention the transition portion has a variable cross-sectional thickness tapering from a thicker-walled end integrally joining the proximal end of the body member to a thin-walled end forming the radiused circumferential shoulder integrally joining the one end of the sleeve-like sealing portion.

Accordingly, one primary feature of the present invention is the provision of an improved sealing member for use with a flexible sleeve-like erection assistance device utilizing a negative pressure to draw the male penis to its anatomic limit within the device.

Another feature of the present invention is the provision of a sealing member that will snugly engage the penile shaft to maintain a seal therewith but which does not grip the penile shaft tightly enough to restrict venous blood return therein.

Still another feature of the present invention is to provide a thin-walled sleeve-like sealing member coaxially aligned with the generally cylindrical hollow body member, the inner circumferential measurement of the sealing member being smaller than the inner circumferential measurement of the body member.

Yet another feature of the present invention is to provide a sleeve-like sealing portion for an erection assistance device the inner circumferential measuremnt of which is a function of the stretched non-erect circumference of the penile shaft.

BRIEF DESCRIPTION OF THE DRAWINGS

In order that the manner in which the above-recited advantages and features of the invention are attained can be understood in detail, a more particular description of the invention may be had by reference to specific embodiments thereof which are illustrated in the appended drawings, which drawings form a part of this specification.

In the drawings:

FIG. 6 is a longitudinal section or sagittal view of the male penile device according to this invention that has an improved sealing member.

FIG. 7 is a partial view in longitudinal vertical cross-section of the sealing member of the device shown in FIG. 6, with the sleeve-like portion rolled back to facilitate insertion of the glans penis.

FIG. 8 is a longitudinal section or saggital view of the male penile device of FIG. 6, showing the sealing member in place when the penis has been fully drawin into the device.

DETAILED DESCRIPTION OF THE INVENTION

Figure 1:
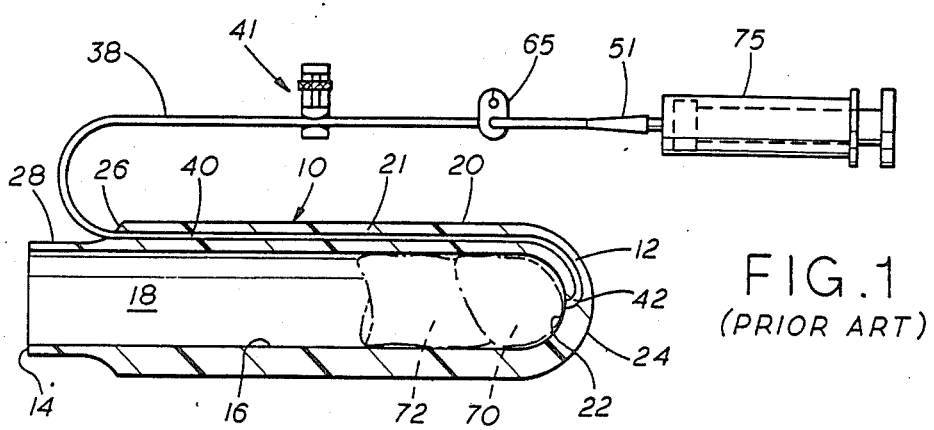
FIG. 1 is a longitudinal section or sagittal view of a male penile device according to U.S. Pat. No. 4,175,554.
Figure 2:
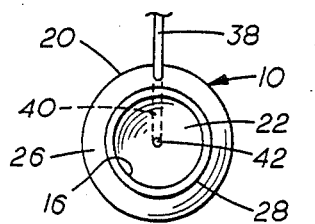
FIG. 2 is an end view of the device depicted in FIG. 1, looking into the interior chamber formed therein.

Referring now to FIGS. 1 and 2, the external male penile device according to U.S. Pat. No. 4,175,554 is shown including a generally penile-shaped, sleeve-like, smooth walled, elastic, relatively soft and pliable hollow cylindrical body 10 with a closed distal end 12 and with an opposing open proximal end 14. An inner surface 16 of body 10 defines a substantially constant-diameter chamber 18 extending from distal end 12 lengthwise through the body 10 to communicate with the outside through opening 14 at the proximal end. Device 10 is formed with a relatively thick wall-section 21 and extends from the most distal end 12 to a preselected location 26 which is in a spaced relation to proximal end 14. Further, distal end 12 includes rounded inner and outer wall surfaces 22 and 24, respectively, with the same preselected thickness as wall-section 21. At a preselected location 26, spaced from proximal end 14, the outer diameter of surface 10 of the body 10 is reduced to define a relatively thin wall-section 28 extending from location 26 to proximal end 14. In an actual device, thin wall-section 28 adjacent its extremity 14 will have a thickness ranging between 0.005 inches and 0.010 inches, thus forming an extremely thin flexible sleeve-like portion.

A flexible, small-diameter evacuation tube 38, having an outer diameter dimension less than the thickness of the thick-wall section of body 10, has portion 40 thereof embedded in thick wall-section 21 with an open end 42 communicating with the interior chamber 18 at the most distal portion of interior rounded end surface 22. The embedded portion of tube 38 enters the thick-wall section 21 proximate the beginning of thin-wall section 28, and extends substantially longitudinally through member 10 to the most distal extremity 12 where the end 42 of tube 38 communicates with the most distal part of interior rounded wall 22, as above described. The remaining free end of tube 38 extends out of the thick-walled section 21 for introducing a negative pressure in the chamber 18.

The thin-wall section 28 adjacent the proximal extremity 14 may be folded back upon itself (not shown), and the glans penis 70, appropriately lubricated, is placed in the rolled-open proximal end of the device 10 and engages the interior surface 16. An appropriate suction or vacuum (negative pressure) is applied to the free extremity 51 of tube 38, which in turn creates a negative pressure within the now sealed interior chamber 18 ahead of the glans penis 70. Such a negative pressure may be applied by any suitable means, like sucking on the end 51 of tube 38 by the wearer or by utilizing a suction device such as a syringe 75. As the negative pressure increases, the lubricated, flaccid penis 27 will be drawn into the hollow interior 18 by the negative pressure and will continue to expand and lengthen in an erection until it reaches its anatomic limit, or until it completely fills the chamber 18 to its most distal end 22.

When the penis is in proper position, the small tube 38 is closed by a clamp 41 or plugged in any convenient manner to prevent air from returning to chamber 18 and interfering with the negative pressure created therein. Thin-wall section 28 of proximal end 14 is then rolled back to its original position so that section 28 now precisely surrounds the proximal shaft portion of the penis 72. The free end of the tubing 38 may be coiled around the thin-walled section 28 and the end tucked into place under another coil of tubing 38 or held in place by a simple conventional cord clamp means 65. This thin-wall section 28 was designed to function as a valve, sealing the inside of the chamber 18 to the penis shaft 72. During sexual intercourse, as the penis 72 moves forward with device 10, the flexible end 28 was to permit a comfortable flexing of proximal end 14 without breaking the seal to the interior of chamber 18. When the penis moved rearward, the thin-walled section 28 was to stretch about the penile shaft 72 for insuring a tight seal.

Figure 3:
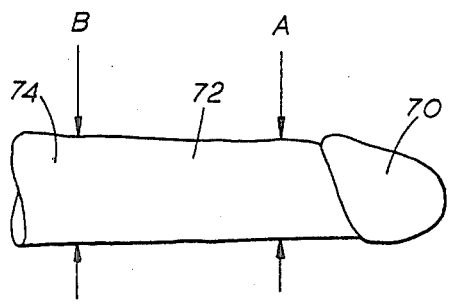
FIG. 3 is a side view of a typical erect male penis.
Figure 4:
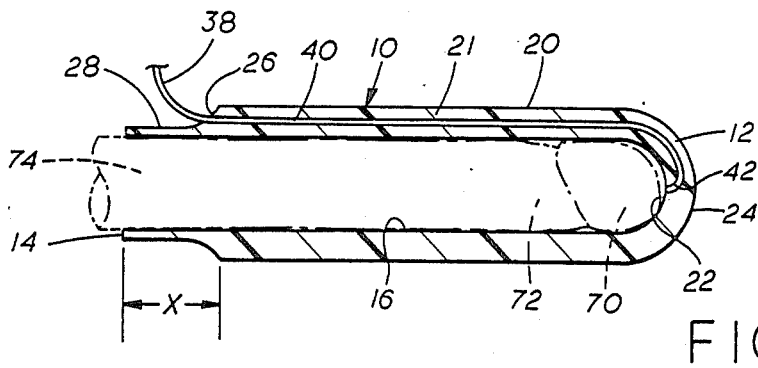
FIG. 4 is a longitudinal section or saggital view of the penile device shown in FIG. 1, showing an assumed fit on an erect penile shaft as shown in FIG. 3.

The operation of prior art device 10 as hereinabove described was based on the typical circumferential measurements of an erect penis 72 as shown in FIG. 3. A circumferential measurement taken at A along the penile shaft behind the glans penis 70 will generally yield a circumferential measurement that is substantially equal to or slightly smaller than a circumferential measurement taken at B along the penile shaft adjacent the proximal end or base of the penis. Therefore, it was assumed that when the penis 72 was drawn to its full anatomic limit into chamber 18 of device 10 (see FIG. 4), that the then erect penis would have a generally uniform erect circumference throughout its length, and possibly even have a slightly larger circumference adjacent the penile shaft base 74. Accordingly, it was believed that the "collar" or thin-walled sleeve-like seal portion 28, having a circumference uniformly equal to the circumferential measurement within chamber 18, would provide the necessary seal in the region "X" when a negative pressure was drawn inside chamber 18 and during the thrusting action during intercourse.

However, it was discovered that in a majority of cases, the seal at the "collar" 28 failed, thus losing the negative pressure inside the chamber 18 of device 10, and also losing the penile erection. It was discovered that as the penis 72 was "stretched" in the initial flaccid condition to its anatomical limit (see FIG. 5), the circumference of the portion of the penile shaft 74 in the "collar" region "X" was actually less than the erect circumferential measurement of the penile shaft within chamber 18. Further, even when the distal end of the penis shaft 72 increased in circumference to fully expand to the circumferential limits of chamber 18 due to the erection, the "stretched" portion of the penile shaft 74 in region "X" never became "erect" and remained flaccid. Therefore, in most cases, there was a "gap" 36 between the penile shaft 74 circumference in the "collar" region "X" of the device 10 and the inner surface of the collar sealing portion 28. This gap 36 caused the sealing collar 28 to fail to seal at all, or it failed with any motion of the penis with respect to the device 10, such as during intercourse.

Further testing and research established that in about 85% of the subjects tested, the "stretched" nonerect circumference was less than the erect circumference for the penile shaft. Data from one set of test measurements is shown in Table I below.

TABLE I

| Number | Stretched Length (Inches) | Stretched Circumference (Inches) | Erect Circumference (Inches) |
|---|---|---|---|
| 2 | 3.0 | 2.75 | 3.0–4.0 |
| 2 | 3.5 | 3.25–3.5 | 3.75–5.0 |
| 2 | 3.75 | 3.5–3.75 | 4.0–5.0 |
| 11 | 4.0 | 2.5–4.5 | 3.0–5.0 |
| 2 | 4.25 | 3.75–4 | 4.5–5.25 |
| 18 | 4.5 | 2.0–4.5 | 2.5–6.0 |
| 3 | 4.75 | 3.0–3.75 | 4.25–4.75 |
| 33 | 5.0 | 2.75–5.5 | 4.0–5.5 |
| 9 | 5.25 | 3.25–5.25 | 4.0–5.0 |
| 32 | 5.5 | 0.5–5.25 | 1.0–5.5 |
| 9 | 5.75 | 3.0–5.0 | 2.5–5.25 |
| 38 | 6.0 | 3.0–5.25 | 3.5–5.5 |
| 7 | 6.25 | 3.0–4.5 | 4.5–5.5 |
| 12 | 6.5 | 3.5–5.5 | 4.5–6.0 |
| 6 | 6.75 | 3.5–5.5 | 4.25–5.5 |

TABLE I-continued

| Number | Stretched Length (Inches) | Stretched Circumference (Inches) | Erect Circumference (Inches) |
|---|---|---|---|
| 11 | 7.0 | 3.25–6.0 | 5.0–5.75 |
| 4 | 7.25 | 4.0–5.5 | 5.25–5.5 |
| 2 | 7.5 | 4.0–5.5 | 5.5–6.25 |
| 1 | 7.75 | 3.25 | 4.75 |
| 1 | 8.25 | 3.5 | 4.75 |

Figure 5:
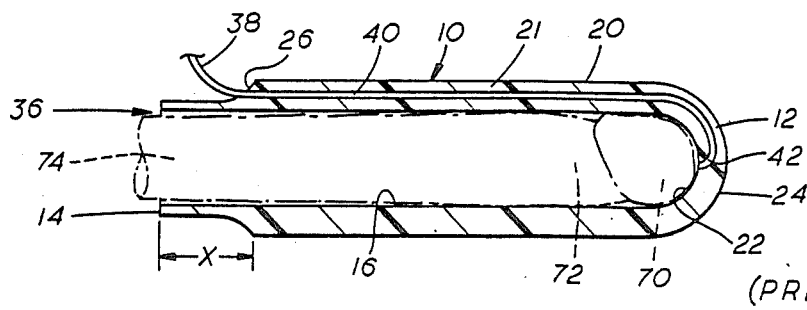
FIG. 5 is a longitudinal section or saggital view of the penile device shown in FIG. 1, showing the most common actual fit of the device on the penile shaft.

Based on the available data and test evidence, it was discovered that the phenomena shown in FIG. 5 was occurring in a majority of cases and the device 10 was not operational in those cases with the prior art design. Accordingly, a new embodiment of the device 10' with an improved sealing member 28' is shown in FIGS. 6–8.

The erection assistance device 10' comprises a generally penile-shaped, sleeve-like, smooth walled, elastic, relatively soft and pliable hollow cylindrical body member 11 with a closed distal end 12 and with an opposing open end 27' integrally joined to one end of a sleeve-like sealing member 28', which has an open proximal end 14'. An inner surface 16 of body member 11 defines a substantially constant-diameter chamber 18 having a predetermined substantially constant circumferential measurement extending from distal end 12 lengthwise through the body member 11 to the point 27' that is the open end of the body member 11.

Device 10' is formed with a relatively thick-wall section 21 between inner surface 16 and outer surface 20. Thick wall-section 21 extends from the most distal end 12 to the end of body member 11 at ridge 27, which is in a spaced relation to proximal end 14' of the sealing member 28'. The body member 11 also includes a tube-retaining collar portion 29 disposed between outer body ridges 26' and 27. After the device 10 has been fully mounted on the penis 72 and an erection achieved, then the tubing 38 can be wrapped circumferentially around the device in the area of collar 29 for storing the tubing during intercourse. The ridges 26' and 27 prevent the tubing from slipping longitudinally on the device during intercourse.

The distal end 12 includes rounded inner and outer wall surfaces 22 and 24, respectively, with the same preselected thickness as wall-section 21. The sealing member 28' includes a thin-walled, flexible, sleeve-like sealing portion 32 that has a substantially constant inner diameter that is less than the inner diameter of body 11 and has a predetermined substantially constant inner circumferential measurement that is less than the circumferential measurement of body 11. The edge of the sleeve-like sealing portion 32 adjacent the open end 14' has a slightly enlarged rounded section 17 for providing additional strength to the open end 14' and to prevent its tearing.

A flexible transition portion 34 integrally interconnects the one end of the sleeve-like sealing portion 32 to the open proximal end 27' of the body member 11. The transition portion 34 positions the sleeve-like sealing portion in a concentric axial alignment with the elongated cylindrical body member 11. The thin-walled, sleeve-like sealing portion 32 between its extreme end 14' and the transition portion 34 will have a thickness ranging between 0.005 inches to 0.010 inches to form an extremely thin, flexible sealing section.

The transition portion 34 also provides a radiused circumferential shoulder 30 extending axially from one end of the sleeve-like sealing portion 32. The transition portion 34 flares outwardly from the shoulder 30 to an increased diameter and thickness to integrally join the open proximal end 27' of body member 11.

The predetermined inner circumferential measurement of chamber 18 in body member 11 is a function of the circumference of the penile shaft 72 in an erect condition and is based on measurements provided by the user. The predetermined inner circumferential measurement of the sleeve-like sealing portion 32 is a function of the circumference of the penile shaft 74 adjacent the penile shaft base in a stretched non-erect condition and is also based on measurements provided by the user. The radius of the outer surface of the cylindrical shoulder 30 is selected to be sufficiently large enough not to injure the erect penis 72 when the penis moves with respect to the body member 11. The predetermined inner circumference of the sleeve-like sealing portion 32 of the sealing member 28 must be chosen to permit a snug engagement with the penis shaft at 74 for functioning as a vacuum seal for inner chamber 18 of body member 11, but not engaging the penis shaft 74 tightly enough to restrict venous blood flow which could injure the penis.

A flexible, small-diameter evacuation tube 38, having an outer diameter dimension less than the thickness of the thick-wall section 21 of body member 11, has a portion 40 embedded in the thick-wall section 21 with an open end 42 communicating with interior 18 of device 10 at the most distal portion 12 of interior rounded surface 22. The embedded portion of tube 38 enters the thick-wall section 21 proximate the ridge 26', and extends substantially lengthwise through body member 11 to the most distal extremity 12 where the end 42 of tube 38 communicates with the most distal part of interior wall 22. The remaining free end of tube 38 extends out of thick-wall section 21 for introducing a negative pressure into chamber 18 as hereinabove described for the device disclosed in FIGS. 1 and 2.

Still referring to FIGS. 6 through 8, the sealing member 28' is folded back over the transition portion 34 and ridge 27 onto the tube-retaining collar portion 29 of body member 11, as particularly shown in FIG. 7. The glans penis 70, appropriately lubricated, is placed in the open rolled proximal end 15' of the sleeve-like sealing member 28' and engages the circumferential shoulder 30. Since the transition portion 34 is flexible, the penis can be forced therethrough, and an appropriate suction or vacuum (negative pressure) is applied to the free extremity 51 (see FIG. 1) of tube 38, which in turn creates negative pressure within the now sealed interior chamber 18 of body member 11 ahead of the glans penis 70. Such a negative pressure may be applied by any suitable means, like sucking on the end 51 of tube 38 by the wearer or by utilizing a suction device such as a syringe 75, as in the prior art device shown in FIG. 1.

As the negative pressure increases, the lubricated, flaccid penis 72 will be drawn into the hollow interior 18 of body member 11 by the negative pressure and will continue to expand and lengthen until it reaches its anatomic limits, or until it completely fills the chamber 18 to its most distal end 22. When the penis is properly positioned, the small tube 38 is clamped by a clamp 41 or plugged in any convenient manner to prevent air from returning to chamber 18 and interfering with the negative pressure created therein as above described for the prior art device shown in FIG. 1.

The sealing member 28' is then rolled back to its original position so that the sealing portion 32 now precisely surrounds the proximal shaft portion 74 of the penis. This thin-wall sleeve-like sealing portion 32 functions as a valve, sealing the inside of the chamber 18 to the penis shaft 74. During sexual intercourse, as the penis 72 moves forward with device 10, the sealing member 28' permits comfortable flexing without breaking the seal to the interior of chamber 18. When the penis 72 is moved rearward, the sealing member 28' stretches about the penis shaft at 74, insuring a tight seal. Since the sealing member 28' has a thickness on the order of 0.005" to 0.010" and is made of an extremely flexible, soft material, any turgescence of the penis 72 can be accommodated by the stretching of the sleeve-like sealing portion 32, thereby accommodating the wearer with a precise, but comfortable, fit.

Numerous variations and modifications may be made in the structure herein described without departing from the present invention. Accordingly, it should be clearly understood that the forms of the invention herein described and shown in the figures of the accompanying drawings are illustrative only and are not intended to limit the scope of the invention.

I claim:

1. An external device for accepting a male penis to its anatomic limit for overcoming impotence and permitting sexual intercourse, comprising:
   a generally cylindrical hollow body member constructed of a flexible and elastic material for accommodating the penis and having distal closed end and a proximal open end, said body member having a first predetermined substantially constant inner circumferential measurement that is a function of the measured circumference of the erect penile shaft,
   a sealing member integrally extending from said proximal open end of said body member and comprising
   a flexible sleeve-like sealing portion having a second predetermined substantially constant inner circumferential measurement which is a function of the measured circumference of the stretched non-erect penile shaft, said second predetermined inner circumferential measurement being less than said first predetermined inner circumferential measurement, and
   a flexible transition portion integrally interconnecting one end of said sleeve-like sealing portion and said open proximal end of said body member for positioning said sleeve-like sealing portion in concentric axial alignment with said body member,
   said sleeve-like sealing portion having a wall thickness substantially less than the wall thickness of said body member and adapted to be rolled up over the open end of the thicker-walled body member to permit the distal end of the male penis to be inserted into said proximal open end of said hollow body member,
   said second predetermined substantially constant inner circumferential measurement of said sealing member sleeve-like sealing portion selected for permitting said sealing portion to snugly contact the exterior surface of the non-erect penile shaft throughout the length of said sleeve-like sealing portion when returned to the unrolled extended position,
   a length of flexible tubing at least a portion of which is disposed longitudinally in the wall of said body member, one end of said tubing communicating with the most distal end of the interior of the hollow body member, the other end of said tubing freely extending from said body member, and means cooperating with said other end of said tubing for evacuating the air from the interior of said body member forward of the inserted penile end for exerting a negative pressure therein for permitting the male penis to expand to its anatomic limit in an erect condition into the interior of the hollow body member, said negative pressure exerted within said body member further acting on said thin-walled sleeve-like portion for collapsing said thin walls about the non-erect portion of the penile shaft in contact with said sealing portion for maintaining an air-tight seal therewith during movement of the penis with respect to said body member during intercourse but not engaging the non-erect penile shaft tightly enough to restrict venous blood flow therein.

2. The device as described in claim 1, wherein said transition portion also provides a radiused circumferential shoulder extending axially from said one end of said sleeve-like sealing portion and flaring outwardly to an increased diameter to join said open proximal end of said body member.

3. The device as described in claim 2, wherein said radiused circumferential shoulder of said transition portion has a radius of sufficient size for providing a smooth rounded surface that will not injure the erect penis.

4. The device as described in claim 2, wherein said transition portion has a variable cross-sectional thickness tapering from a thicker-walled end integrally joining said proximal end of said body member to a thin-walled end forming said radiused circumferential shoulder integrally joining said one end of said sleeve-like sealing portion.

5. In an external device for accepting a male penis to its anatomic limit for overcoming impotence and permitting sexual intercourse, including a generally cylindrical flexible hollow body member having a distal closed end and a proximal open end for accommodating the male penis, the body member having a sustantially constant inner circumferential measurement, and a means for introducing a negative pressure into the hollow body member through its distal end, the improvement comprising a sealing member integrally extending from said proximal open end of said body member and comprising a flexible sleeve-like sealing portion having a predetermined substantially constant inner circumferential measurement which is a function of the measured circumference of the stretched non-erect penile shaft, said predetermined inner circumferential measurement being less than said inner circumferential measurement of said body member, and a flexible transition portion integrally interconnecting one end of said sleeve-like sealing portion and said open proximal end of said body member for positioning said sleeve-like sealing portion in concentric axial alignment with said body member, said sleeve-like sealing portion having a wall-thickness substantially less than the wall-thickness of said body member and adapted to be rolled up over said transition portion onto the thicker-walled body member to permit the distal end of the male penis to be inserted into the proximal end of said hollow body member, said second predetermined substantially constant inner circumferential measurement of said sealing member sleeve-like sealing portion selected for permitting said sealing portion to snugly contact the exterior surface of the non-erect penile shaft throughout the length of said sleeve-like sealing portion when returned to the unrolled extended position, said negative pressure exerted within said body member further acting on said thin-walled sleeve-like portion for collapsing said thin walls about the non-erect portion of the penile shaft in contact with said sealing portion for maintaining an air-tight seal herewith during movement of the penis with respect to said body member during intercourse but not engaging the non-erect penile shaft tightly enough to restrict venous blood flow therein.

6. The device as described in claim 5, wherein said transition portion also provides a radiused circumferential shoulder extending axially from said one end of said sleeve-like sealing portion and flaring outwardly to an increased diameter to join said open proximal end of said body member.

7. The device as described in claim 6, wherein said radiused circumferential shoulder of said transition portion has a radius of sufficient size for providing a smooth rounded surface that will not injure the erect penis.

8. The device as described in claim 6, wherein said transition portion has a variable cross-sectional thickness tapering from a thicker-walled end integrally joining said proximal end of said body member to a thin-walled end forming said radiused circumferential shoulder integrally joining said one end of said sleeve-like sealing portion.

* * * * *